(12) United States Patent
Kasinkas et al.

(10) Patent No.: US 6,200,307 B1
(45) Date of Patent: Mar. 13, 2001

(54) TREATMENT OF IN-STENT RESTENOSIS USING CYTOTOXIC RADIATION

(75) Inventors: Michael Kasinkas, Plymouth; Robert A. Van Tassel, Excelsior, both of MN (US)

(73) Assignee: Illumenex Corporation, Plymouth, MN (US)

( * ) Notice: Subject to any disclaimer, the term of this patent is extended or adjusted under 35 U.S.C. 154(b) by 0 days.

(21) Appl. No.: 09/083,358

(22) Filed: May 22, 1998

Related U.S. Application Data

(60) Provisional application No. 60/047,383, filed on May 22, 1997.

(51) Int. Cl.[7] ............................................. A61B 18/18
(52) U.S. Cl. ............................ 606/7; 606/15; 606/191; 606/194
(58) Field of Search ...................... 606/2, 3, 7, 10, 606/13–16, 191–195; 607/88, 89, 92, 93

(56) References Cited

U.S. PATENT DOCUMENTS

| | | | |
|---|---|---|---|
| 4,512,762 | 4/1985 | Spears | 604/21 |
| 5,053,033 | 10/1991 | Clarke | 606/3 |
| 5,092,841 | * 3/1992 | Spears | 604/96 |
| 5,100,429 | * 3/1992 | Sinofsky et al. | 606/195 |
| 5,116,864 | 5/1992 | March et al. | 514/455 |
| 5,254,112 | 10/1993 | Sinofsky et al. | 606/7 |
| 5,514,707 | 5/1996 | Deckelbaum et al. | 514/455 |
| 5,591,199 | * 1/1997 | Porter et al. | 606/198 |
| 5,620,438 | 4/1997 | Amplatz et al. | 606/10 |
| 5,899,917 | * 5/1999 | Edwards et al. | 606/195 |
| 5,925,035 | * 7/1999 | Buckley et al. | 606/7 |

FOREIGN PATENT DOCUMENTS

WO 9607451    3/1996    (WO).

* cited by examiner

*Primary Examiner*—Linda C. M. Dvorak
*Assistant Examiner*—Bryan K. Yarnell
(74) *Attorney, Agent, or Firm*—Thomas J. Engellenner; Nutter, McClennen & Fish, LLP

(57) ABSTRACT

A method for treating in-stent restenosis using radiation having a wavelength sufficient to kill or promote cellular death (e.g., through programmed cell death), or otherwise remove smooth muscle cells which have proliferated, or which might otherwise proliferate, in the proximity of (i.e., within, around or adjacent to) a stent within a body lumen, causing (or potentially causing) at least partial blockage of the lumen. The treatment method includes irradiating smooth muscle cells in the region of the stenosis with non-ablative, cytotoxic radiation, such as UV radiation. A cytotoxic, photoactivatable chromophore may also be delivered to the treatment site prior to irradiation. The method can be used prophylactically or to treat in-stent restenosis after blockage has occurred without further damage to surrounding tissue.

10 Claims, 3 Drawing Sheets

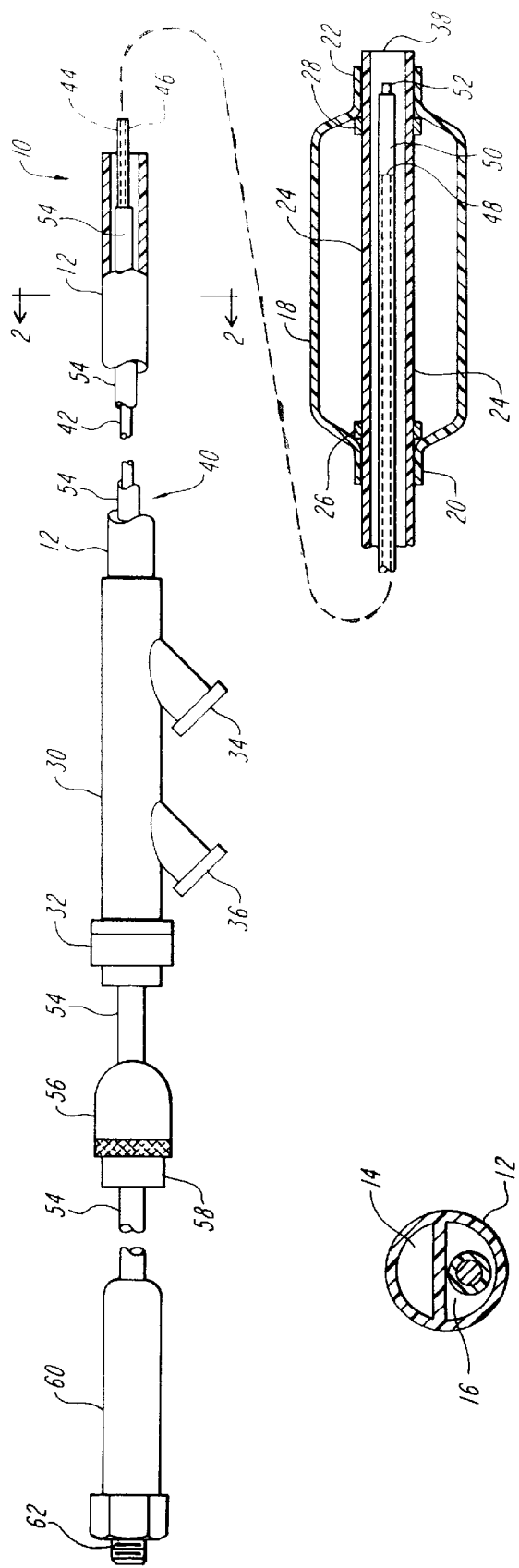

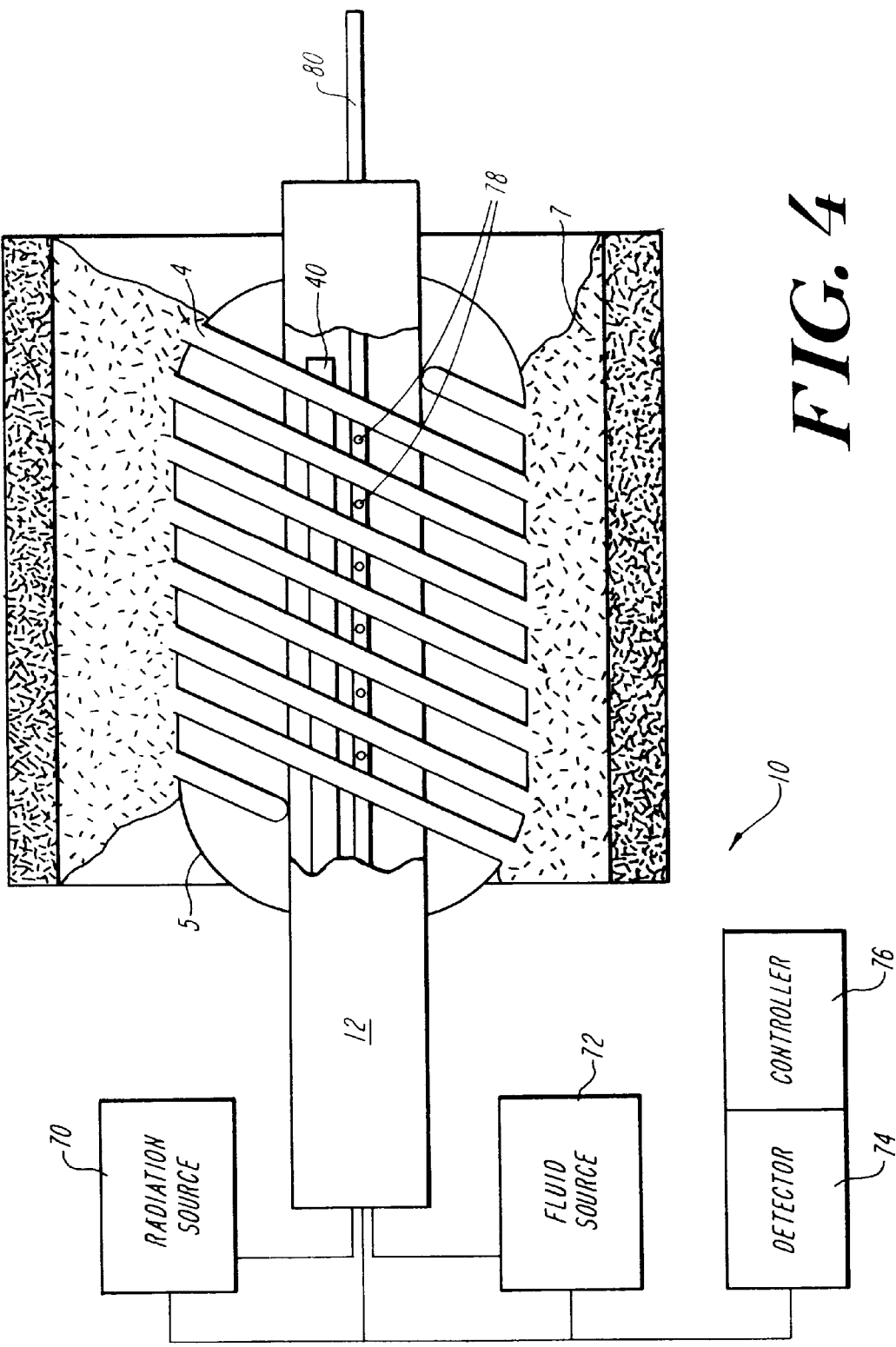

TREATMENT OF IN-STENT RESTENOSIS USING CYTOTOXIC RADIATION

REFERENCE TO RELATED APPLICATION

The present application claims the benefit of, and incorporates by reference, the commonly owned, co-pending U.S. provisional application Ser. No. 60/047,383, filed May 22,1997.

BACKGROUND OF THE INVENTION

The present invention concerns methods and systems for treatment of restenosis in body lumens such as blood vessels and, in particular, the treatment of in-stent restenosis.

Endoluminal stents are commonly used to treat obstructed or weakened body lumens, such as blood vessels and other vascular lumens. Numerous stents exist for this purpose, including those made of metals, fibers and other biocompatible materials. In general, the stent is either formed outside the body and then guided into place (e.g., adjacent to an obstruction) through a body lumen, or is positioned into place prior to formation and is then expanded and/or formed in situ within the body lumen. Once deployed, the stent can remain in the body lumen where it will maintain the patency of the lumen and/or support the walls of the lumen which surround it.

One factor impeding the success of stent technology in endoluminal treatments is the frequent occurrence of in-stent restenosis, characterized by proliferation and migration of smooth muscle cells within and/or adjacent to the implanted stent, causing reclosure or blockage of the body lumen. While the reasons for such smooth muscle cell proliferation following stent implantation are not entirely clear, it is believed that positioning of the stent within the body lumen may somehow irritate or damage the surrounding lumen walls and activate medial smooth muscle cells lining the walls.

Current methods for treating endoluminal restenosis, such as that which occur within or around a stent, generally consist of invasive procedures which physically remove atherosclerotic plaque by, for example, shaving or ablating the plaque, or by implanting a second stent. However, these procedures can cause further damage to the area of treatment and/or initiate further smooth muscle cell proliferation.

Accordingly, it is an object of the present invention to provide a substantially non-invasive method of treating in-stent restenosis by applying radiation to the smooth muscle cells which have grown within or around a stent implant in a manner that does not substantially damage the surrounding lumen wall or the stent itself, while resulting in a reduction of smooth muscle cell mass.

SUMMARY OF THE INVENTION

Methods and systems are disclosed for treating in-stent restenosis using radiation having a wavelength sufficient to kill or promote cellular death (e.g., through programmed cell death), or otherwise remove smooth muscle cells which have proliferated, or which might otherwise proliferate, in the proximity of (i.e., within, around or adjacent to) a stent within a body lumen, causing (or potentially causing) at least partial blockage of the lumen. Devices are disclosed for providing such therapeutic radiation at the stent with or without concurrent mechanical (e.g. balloon dilation) angioplasty. Treatment methods are also disclosed which include irradiating smooth muscle cells in the region of the stenosis with non-ablative, cytotoxic radiation, such as UV radiation.

A cytotoxic, photoactivatable chromophore may also be delivered to the treatment site prior to irradiation. The methods and systems can be used prophylactically or to treat in-stent restenosis after blockage has occurred without further damage to surrounding tissue.

In-stent restenosis can be treated effectively and with minimal tissue damage using cytotoxic, nonablative radiation, such as UV radiation. The radiation kills or otherwise inactivates smooth muscle cells which have proliferated or are susceptible to proliferation within and/or adjacent to a stent in a body lumen, causing the cells to retract from the stenosed region. The radiation is preferably delivered to the area around (e.g., within or adjacent to) the stent via an optical fiber or other waveguide incorporated, for example, into a percutaneous catheter.

The term "in-stent restenosis," as used herein, includes partial or complete blockage of a body lumen in an area of stent implantation due in whole or in part to proliferation of medial smooth muscle cells within or around (e.g., adjacent to) the stent. The term "cell overgrowth" as used herein is intended to describe any condition involving the proliferation of cells in proximity to a stent. The term "body lumen," as used herein, includes any body lumen capable of containing a tent, such as vascular, urological, biliary, esophageal, reproductive, endobronchial, gastrointestinal, and prostatic lumens. The term "non-ablative, cytotoxic radiation," as used herein, means radiation which directly or indirectly (e.g., by apoptosis) kills or otherwise causes the removal of smooth muscle cells in a stenosed region, resulting in a reduction in tissue mass and/or an increase in the diameter of the lumen, without the use of heat ablation.

In one embodiment of the invention, the cytotoxic, non-ablative radiation is ultraviolet (UV) radiation having a wavelength of less than about 280 nanometers, down to about 240 nanometers (due to the limited transmission efficiency of glass optical fibers at lower wavelengths). The effect of UV radiation having this wavelength range, commonly known as UV "C" radiation, at the doses necessary to penetrate the build up of smooth muscle cell mass, causes direct cellular death of most cells and can cause programmed cell death in other cells, resulting in a reduction in cell mass without heating or damaging the surrounding tissue.

In another embodiment of the invention, the cytotoxic, non-ablative radiation has a longer wavelength, such as UV "A" or "B" radiation in the wavelength range of about 280 nanometers to 400 nanometers, or visible radiation having a wavelength of about 400 to 700 nanometers, or infrared radiation from about 700 nanometers to 2.6 micrometers, and is used in conjunction with a photoactivatable, cytotoxic chromophore which is activated upon exposure to light at some or more of these wavelengths. The term "photoactivatable, cytotoxic chromophore," as used herein, encompasses chromophores capable of being absorbed by mammalian tissues and being activated upon exposure to light so cells of the tissue die or cease to proliferate. In the present invention, the photoactivatable chromophore is delivered to tissue which has increased in mass (e.g., due to smooth muscle cell proliferation) within or around a stent and is causing restenosis of the lumen supported by the stent. The tissue is then exposed to radiation of a sufficient wavelength to activate the chromophore. Once activated by the light, the chromophore causes direct programmed death (apoptosis) thereby decreasing the number of cells and the mass of the tissue.

Suitable chromophores for use in the invention are generally selected for absorption of light that is deliverable from common radiation sources (e.g. UV light ranging from 240–400 nanometers, or visible light having wavelengths of 400 nanometers or longer). For example, photoactivatable psoralens and hematoporphyrins can be administered systemically or locally to the stenosed region prior to irradiation, thereby rendering smooth muscle cells in the region more susceptible to radiation. Other suitable chromophores are well known in the art and include those which are photoactivated upon irradiation with either long-wave UV light (PUVA) (See, e.g., U.S. Pat. No. 5,116,864 (Mar. et al.) or with visible light (see, e.g., U.S. Pat. No. 5,514,707 (Deckelbaum et al.), the disclosures of which are incorporated herein by reference.)

Various radiation sources can be use in accordance with the present invention to deliver non-ablative, cytotoxic radiation to a stenosed region within or around a stent. Generally, the radiation is delivered via a laser catheter carrying a fiber optic waveguide. Either pulsed or continuous wave ("CW") lasers can be used in the present invention, and the lasant medium can be gaseous, liquid or solid state. The laser can be a pulsed excimer laser, such as a KrF laser. Alternatively, rare earth-doped solid state lasers, ruby lasers and Nd:YAG lasers can be operated directly or in conjunction with frequency modification means to produce an output beam at the appropriate radiation wavelength (e.g., UV wavelength). Alternatively, a UV flash lamp can be employed.

In one embodiment, a laser system which operates at about 266 nanometers is used to maximize the cytotoxic effect of the radiation. This may be achieved using an output beam wavelength of about 266 nanometers or, alternatively, using an output beam wavelength of about 1064 nanometers, such as a common Nd:YAG laser, in conjunction with two doubling crystals to yield a radiation output of about 266 nanometers. Similarly, a Nd:YLF laser operating at about 1047 nanometers can be used in conjunction with two frequency doubling crystals. Other useful UV radiation sources include, for example, Argon ion lasers emitting UV light at about 257 or 275 nanometers and KrF excimer lasers emitting light at about 248 nanometers.

In another embodiment of the invention, the cytotoxic, non-ablative radiation is provided by a "low energy" radiation source. The term "low energy" is used herein to describe both laser and non-coherent radiation systems having an energy output of less than about 5 $J/cm^2$ per pulse for pulsed lasers, or a total dose of less than about 1000 $J/cm^2$, more preferably less than 100 $J/cm^2$, for continuous wave lasers or non-coherent radiation sources.

In general, when using conventional percutaneous catheters to deliver radiation, at least one optical fiber or waveguide is incorporated into the catheter for transmission and delivery of the radiation to the lesion (i.e., stenosed) site. For example, an optical fiber having about a 200 micron diameter core may be used. The catheter tip can also contain focusing optics or diffusive elements for use in directing the radiation emitted from the catheter within an artery. The therapeutic radiation can be provided by a single laser or a plurality of lasers operating in tandem to deliver cytotoxic, nonablative laser radiation.

Catheter systems useful in connection with the present invention may also be equipped with a translucent (light-conducting) balloon which encompasses the optical fiber(s) or other energy conducting means. One example of such an apparatus is disclosed in commonly-owned, U.S. Pat. No. 5,620,438 issued to Amplatz et al. on Apr. 15, 1997 and incorporated herein by reference. Once the catheter is guided into place within or adjacent to an area of restenosis associated with a stent, the balloon is inflated to dilate the surrounding tissue. Light is then delivered into the balloon via the optical fiber(s) and is transmitted through the balloon onto the surrounding tissue of the lumen walls. The balloon is preferably large enough in diameter to completely cover (i.e., come in contact with all portions of) the stenosed region. Preferably, the balloon is at least sized such upon inflation, it extends beyond the length of the stent by a distance sufficient to dilate any blockage within the stent. The light source (or sources) can likewise be chosen to extend beyond the stent by a sufficient distance to ensure treatment of the entire restenosis. In one illustrated embodiment, a 30 mm length balloon is inflated within a 20 mm stent overgrown (infiltrated) with smooth muscle cells. The balloon is inflated so that the entire interior of the stent is dilated and the distal ends of the balloon emerge from the stent.

The method of the present invention can be used to treat in-stent restenosis which has already occurred within or adjacent to a stent in a body lumen. The method provides the advantage of being substantially non-invasive and non-injurious compared to methods which physically remove or ablate endoluminal lesions.

The invention will next be described in connection with certain illustrated embodiments. However, it should be clear that various changes and modifications can be made by those skilled in the art without departing from the spirit or scope of the invention.

BRIEF DESCRIPTION OF THE DRAWINGS

FIG. 1 is a partially cross-sectioned side view of a surgical instrument useful in accordance with the present invention;

FIG. 2 is cross-sectional front view taken along the line 2—2 in FIG. 1:

FIG. 4 is a schematic illustration of the balloon catheter device shown in FIG. 3 in operation.

DETAILED DESCRIPTION

Figure 3:
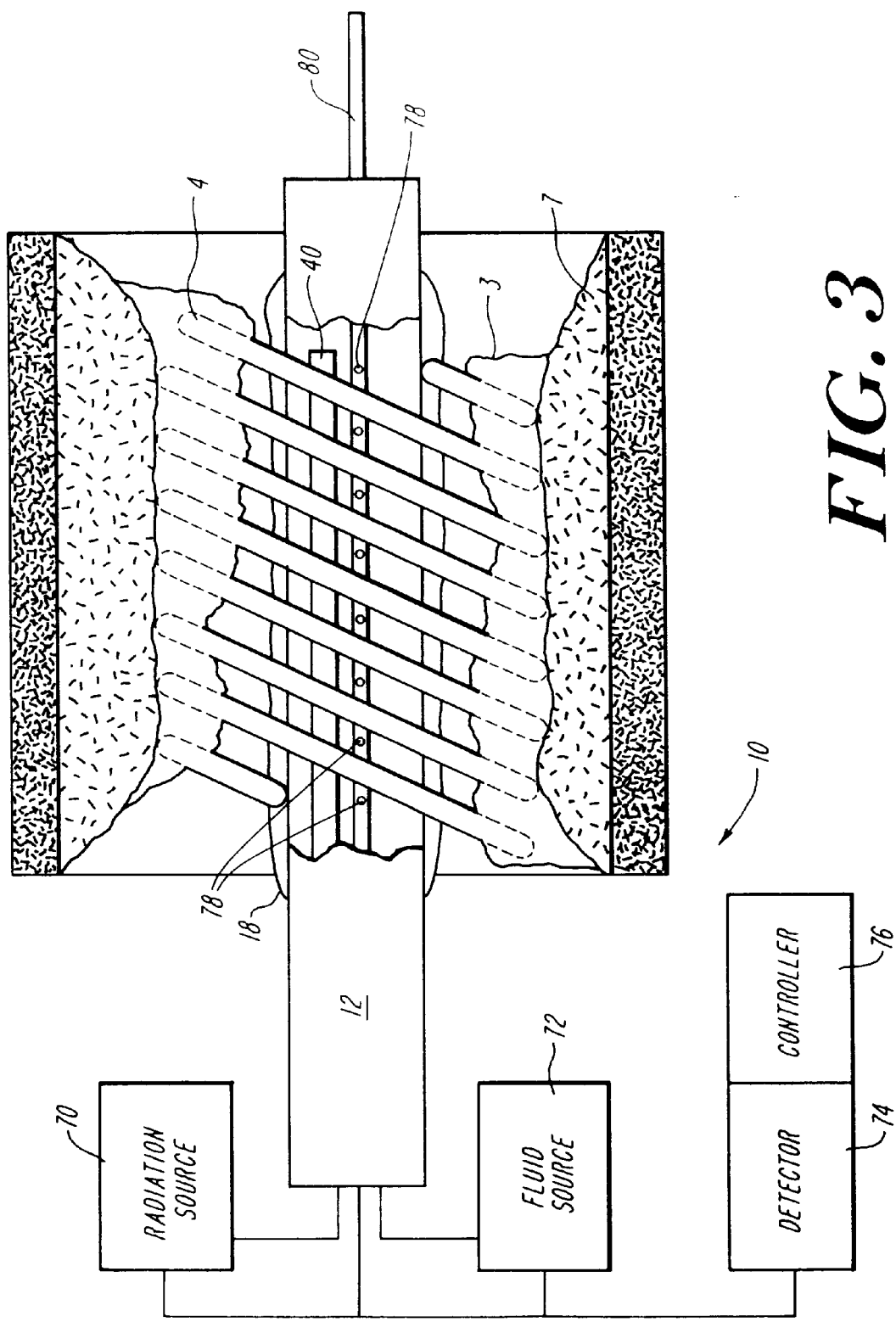
FIG. 3 is a schematic cross-sectional illustration of a balloon catheter device according to the present invention positioned within a stent exhibiting partial restenosis.

FIG. 1 illustrates an instrument 10 especially designed for delivering radiant energy to an in-stent restenosis site within the vascular system of a patient. It is seen to comprise a elongated, flexible tubular catheter body 12 having an outer diameter of about 0.040 in. and a wall thickness of approximately 0.005 in. The catheter body is preferably extruded from polyethylene plastic and, as is illustrated in the cross-sectional front view of FIG. 2, has at least first and second lumens 14 and 16, respectively.

Appropriately joined to the exterior surface of the tubular body 12 at its distal end portion is an expansion element 18, such as a balloon, which can circumferentially bonded at its ends 20 and 22 to the tube 12 at spaced apart locations. The expansion element 18 can be mechanically expandable but is preferably formed from polyethylene or polytetrafluoroethylene structure which can be expanded by inflation. These plastics exhibiting high radiant energy transmissivity in the UV light portion of the spectrum. The length of the expansion element is preferably chose to be at least as great or greater than the stent to be treated. The expansion element 18 may typically be anywhere from 20 to 30 mm in length and can span one or more ports 24 formed through the first lumen 14 (FIG. 2), i.e., the inflation lumen. It is also found expedient to locate radioopaque marker bands 26 and 28 on opposite ends of the expander member relative to a lesion to be treated under fluoroscopy.

Disposed at the proximal end of the catheter body 12 is a molded plastic hub member 30 which is generally tubular and which has a Touchy-Borst type compression fitting 32 disposed near its proximal end. The hub 30 also includes first and second ports 34 and 36 having Luer fitting for connection to liquid supply tubes (not shown). The port 34 is in fluid communication with the inflation lumen 14 and when a fluid, such as normal saline, is injected under pressure into that port, it flows through the lumen 14 and the ports 24 in the catheter to affect inflation of the expansion element 18. The port 36 is in fluid communication with the lumen 16 catheter. By pumping saline with a roller pump at a low rate of about 2–4 cubic cms per minute into the port 36, the flow prevents blood from entering the distal end 38 of the catheter.

Extending through the compression fitting 32, the tubular hub 30 and through the second lumen 16 of the instrument 10 is an elongated, flexible, radiant energy-transmissive fiber assembly 40. Where the radiation source to be employed is a source of UV light, the radiant energy transmissive fiber may comprise a core member 42 including a quartz fiber 44 covered by a Teflon jacket 46. The wall thickness of the jacket may be approximately 0.003 in. The quartz fiber has a distal end 48 and the jacket 46 extends in the distal direction beyond the end 48 of the fiber for a distance of about 6 mm and forms a radiant energy diffusing and emitting element 50. A radioopaque plug 52 is fitted into the distal end of the element 50.

Starting a predetermined distance proximal of the distal plug 52 and extending proximally through the compression fitting 32 of the hub 30 is an outer tubular reinforcing member 54, which preferably comprises a stainless steel tube whose O.D. is about 0.014 in. The stainless steel reinforcing member 54 tightly surrounds the jacket 46 of the quartz fiber 44 and because of its relative rigidity compared to that of the quartz fiber 44, it permits the radiant energy transmissive fiber assembly 40 to be pushed longitudinally through the lumen 16 of the catheter body 12 when a force is applied at the proximal end of the radiant energy transmissive fiber assembly. The length of the core 42 that extends beyond the distal terminus of the reinforcing member 54 may be approximately 13 in. and, as such, the assembly 40 exhibits sufficient "pushability" and "torqueability" to permit the unreinforced portion to transverse the lumen 16 of the tubular body 12. If gamma radiation is to be delivered to the affected area of the blood vessel, a suitable source of gamma radiation, such as cobalt 60 particles may be embedded in the plastic at the distal end of an elongated flexible fiber.

With continued reference to FIG. 1, there is shown attached to the portion of the radiant energy-transmissive fiber assembly 40 extending proximally beyond the compression fitting 32 and adjustable stop member 56. The stop assembly 40 to a desired position and then locked in place by rotating the knurled grip 58, thereby effectively establishing a predetermined travel distance between the stop member 56 and the proximal end of the hub 30. This also defines the extent of displacement of the diffusing element 50 in the distal direction.

The radiant energy-transmissive fiber assembly 40 extends proximally beyond the stop member 56 and passes through a strain relief member 60, terminating in a standard connector 62. Connector 62 is adapted to couple with the output of a radiant energy source (not shown). The radiant energy source is preferably a pulsed or continuous wave laser capable of producing an output beam at an appropriate UV wavelength. It has been found that a wavelength in the range of from 240 nm to 280 nm covers the range exhibiting efficacy in inhibiting smooth muscle tissue growth.

The UV light emanating from the laser source passes through the quartz fiber 44 to its distal end 48. The Teflon diffusing element 50, comprising the jacket extension, is found to uniformly diffuse the UV light exiting the end of the quartz fiber. Because the tubular body 12 and the expander member 18 are fabricated from a highly UV light transmissive material (polyethylene), the UV light emanating from the diffuser 50 causes a radial band of light, approximately the length of the jacket extension, to radiate out through the expander member to impinge upon the intimal tissue. By controlling the displacement of the fiber in the axial direction, the emanating band of UV radiation can be made to traverse the entire length of the expander member continuously or in discrete steps to thereby expose the adjacent vessel wall to the radiant energy. Various radiation diffusive tip assemblies can also be employed in conjunction with the present invention, such the diffuser designs disclosed in International Patent Application Pub. No. WO 96/07451 published Mar. 14, 1996 and incorporated herein by reference. It is possible, of course, also to rotate the radiant energy transmissive fiber assembly within the lumen of the catheter when and if the radiation pattern exiting the diffusing member is not annularly symmetrical.

The methods of the present invention can be practiced as shown in FIG. 3, where radiation delivered via a catheter instrument (such as instrument 10 described above in FIGS. 1–2 or a similar balloon catheter instrument 12 adapted to include a radiation-emitter). In use, the instrument 10 serves to treat restenosis 3 which has occurred (e.g., due to smooth muscle cell overgrowth) within and adjacent to a stent 4 situated in a region of a body lumen 7.

The instrument 10 includes an elongated flexible tube 12 with an expandable balloon 18 attached at the distal end. The overall system can further include a radiation source 70, a fluid source 72 (for balloon inflation and/or blood stream perfusion), a diagnostic detector 74, and a controller 76 (e.g., a microprocessor which controls the other elements by either preprogrammed instructions or real-time diagnostic or user-generated instructions). The catheter also includes at least one optical fiber assembly 40 for delivering radiation into the balloon 18. At its proximal end, the optical fiber assembly is connected to a source of radiation 70, such as a laser. The instrument 10 can further include one or more sensors 78 (e.g., ultrasonic probes or electrical mapping electrodes) which are electronically or optically coupled to the detector 74 to provide data on the progress of the dilation, irradiation or other conditions in-situ.

Suitable lasers for delivering radiation are described, for example, in U.S. Pat. No. 5,053,033, the disclosure of which is incorporated by reference herein. The optical fiber 40 extends through the catheter body 12 into the balloon 18 attached to the distal end. The tip of the fiber is preferably designed to diffuse light outwardly through the balloon, for example, by tapering the end or by using a diffusive radio-opaque material, as is well known in the art.

The radiation source 70 can be a UV light source which delivers light having a wavelength ranging from about 200 to about 400 nanometers, more preferably from about 240 to about 370 nanometers. The radiation can be provided by a variety of sources, including non-coherent UV light sources and excimer laser sources (e.g., a KrF excimer laser operating at 248 nanometers or an Argon ion laser at 257 or 275 nanometers). Alternatively, the source can be a visible light source which delivers light having a wavelength greater than 400 nanometers, preferably around 420 nanometers. The energy of the UV radiation can be about 5 J/cm$^2$ per pulse or less for pulsed lasers, or a total dose of about 1000 J/cm$^2$ or less. The power density of the radiation is preferably less than 5 watts per square centimeter, more preferably less than 2 watts per square centimeter.

The use of the catheter system shown in FIG. 3 is further schematically illustrated in FIG. 4. The catheter 12 is first guided into place adjacent to an area of smooth muscle cell overgrowth within a stent using, for example, a conventional guidewire 80. The inflatable balloon 18 is then expanded which applies pressure against the surrounding lumen wall 7. Expansion of the inflatable balloon 18 serves to dilate the obstructed area and increase the uniformity of light distribution onto the surrounding tissue.

Following expansion of the inflatable balloon 18, radiation from the radiation source 70 is delivered via one or more assemblies of optical fibers 40 which extend through the terminal end of the device into the inflatable balloon 18. In one embodiment, a diffusive radio-opaque tip is attached to the terminal end through which the radiation is delivered and scattered throughout the inflatable balloon 18. The light delivered through the inflatable balloon 18 is then absorbed by cells of the surrounding tissue, causing death or inactivation of the cells such that a reduction occurs in the mass of the tissue (e.g., the diameter of the stenosed lumen increases).

In one embodiment, a photoactivatable chromophore, such as a psoralen (e.g., 8-methoxypsoralen), is delivered either locally or systemically to the treatment area 3 (See FIG. 3) prior to irradiation. The chromophore is then activated by exposure to light (e.g., visible light having a wavelength of about 420 nanometers when using 8-methoxypsoralen) and causes death of the cells in the treatment removal of the catheter device from the stenosed region, a reduction in cell mass is observed in the treatment area.

Although the illustrated embodiments describe a system in which the balloon and irradiation means of the present invention are structurally distinct (with the balloon element 18 bonded directly to the catheter body 12 and the light-emitting fiber carried within an internal lumen 16 of the catheter body 12), it should be clear that a combined balloon and light fiber instrument can be substituted to achieve the same effect. Such an instrument (with a light emitter of an appropriate length and an appropriately sized balloon) can be constructed, for example, by following the teachings of U.S. Pat. No. 4,512,762 issued to Spears on Apr. 23, 1985 and incorporated herein by reference. Alternatively, the methods of the present invention can be practiced without a dilation balloon employing a simple radiationemitting catheter such as that disclosed in U.S. Pat. No. 5,254,112 issued to Sinofsky et al. on Oct. 19, 1993 or U.S. Pat. No. 5,0553,033 issued to Clarke on Oct. 1, 1991, both of which are also incorporated herein by reference.

Those skilled in the art will be able to recognize, or be able to ascertain using no more than routine experimentation, numerous other equivalents to the specific devices and procedures described herein. Such equivalents are considered to be within the scope of this invention and are covered by the following claims.

What we claim is:

1. A method of treating restenosis which has occurred in proximity to a stent that has previously been implanted in a body lumen comprising:

disposing an optical waveguide means inside the body lumen containing the stent;

locating the waveguide means adjacent to an area in which smooth muscle cell overgrowth in the proximity of the stent has occurred; and irradiating the area of smooth muscle cell overgrowth with non-ablative, cytotoxic radiation via said optical waveguide means.

2. The method of claim 1 wherein the radiation is UV radiation.

3. The method of claim 2 wherein the UV radiation is low power UV radiation.

4. The method of claim 1 wherein the radiation has a wavelength of about 240 to about 280 nanometers.

5. The method of claim 2 wherein the UV radiation has power density of about 5 watts per square centimeter or less.

6. The method of claim 1 wherein the method further comprises delivering a chromophore to the area of smooth muscle overgrowth prior to irradiation.

7. The method of claim 6 wherein the chromophore is a photoactivatable psoralen.

8. The method of claim 6 wherein the radiation is selected from the group consisting of UV radiation and visible radiation.

9. The method of claim 1 wherein the step of irradiating the area of smooth muscle cell overgrowth results death of at least a portion of the cells in the area of overgrowth, resulting in decreased tissue mass and an increase in the diameter of the lumen containing the overgrowth.

10. The method of claim 1 wherein the method further comprises the step of deploying an expansion element within the stent to mechanically displace blockage within the stent.

* * * * *

UNITED STATES PATENT AND TRADEMARK OFFICE
CERTIFICATE OF CORRECTION

PATENT NO. : 6,200,307 B1  
DATED : March 13, 2001  
INVENTOR(S) : Michael Kasinkas and Robert A. Van Tassel Page 1 of 1

It is certified that error appears in the above-identified patent and that said Letters Patent is hereby corrected as shown below:

Column 2,  
Line 24, reads "a tent, such as vascular," should read -- a stent, such as vascular --

Column 3,  
Line 10, reads "U.S. Pat. No. 5,116,864 (Mar. et al.) should read -- U.S. Pat. No. 5,116,864 (March et al.) --

Signed and Sealed this

Twenty-sixth Day of March, 2002

*Attest:*

JAMES E. ROGAN  
*Director of the United States Patent and Trademark Office*

*Attesting Officer*